US006648923B1

(12) United States Patent
Goettel et al.

(10) Patent No.: US 6,648,923 B1
(45) Date of Patent: Nov. 18, 2003

(54) COMPOSITIONS CONTAINING 1,4-DIAMINO-2-METHOXYMETHYLBENZENE AND SALTS THEREOF AND METHODS FOR DYEING KERATIN FIBERS WITH SAME

(75) Inventors: Otto Goettel, Marly (CH); Aline Pirrello, Givisiez (CH); Andre Hayoz, Senedes (CH); Hans-Juergen Braun, Ueberstorf (CH)

(73) Assignee: Wella Aktiengesellschaft, Darmstadt (DE)

( * ) Notice: Subject to any disclaimer, the term of this patent is extended or adjusted under 35 U.S.C. 154(b) by 104 days.

(21) Appl. No.: 09/659,270

(22) Filed: Sep. 12, 2000

(30) Foreign Application Priority Data

Nov. 29, 1999 (DE) .......................................... 199 57 282

(51) Int. Cl.⁷ ................................................ A61K 7/13
(52) U.S. Cl. ....................... 8/405; 8/405; 8/406; 8/410; 8/421; 8/426; 8/437
(58) Field of Search ............................ 8/405, 406, 410, 8/421, 426, 437

(56) References Cited

U.S. PATENT DOCUMENTS

| | | | | |
|---|---|---|---|---|
| 2,273,564 A | * | 2/1942 | Dickey et al. .............. | 266/574 |
| 4,152,112 A | | 5/1979 | Bugaut et al. ................ | 8/10.2 |
| 4,311,478 A | | 1/1982 | Bugaut et al. ................ | 8/407 |
| 5,919,273 A | * | 7/1999 | Rondeau et al. ............. | 8/407 |

FOREIGN PATENT DOCUMENTS

WO 99/11228 3/1999

OTHER PUBLICATIONS

Analogie Zu W/R/ Baker, J. Org. Chem. 1983, 48, pp. 5140–5143.

* cited by examiner

Primary Examiner—Yogendra N. Gupta
Assistant Examiner—Eisa Elhilo
(74) Attorney, Agent, or Firm—Michael J. Striker

(57) ABSTRACT

The aqueous or aqueous-alcoholic oxidative dye precursor composition includes 1,4-diamino-2-methoxymethylbenzene, or a physiologically compatible salt thereof, as developer substance and one or more conventional coupler compounds. A ready-to-apply hair dyeing mixture having a pH of 6 to 10.5 is made by mixing the aqueous or aqueous-alcoholic oxidative dye precursor composition with an oxidizing agent, such as 6% hydrogen peroxide in a weight ratio of 5:1 to 1:3. The compositions may also contain conventional cosmetic additive ingredients and direct-dyeing dye compounds.

13 Claims, No Drawings

COMPOSITIONS CONTAINING 1,4-DIAMINO-2-METHOXYMETHYLBENZENE AND SALTS THEREOF AND METHODS FOR DYEING KERATIN FIBERS WITH SAME

BACKGROUND OF THE INVENTION

1. Field of the Invention

The subject matter of the present invention is a method for making 1,4-diamino-2-methoxymethylbenzene and physiologically compatible salts thereof. It also includes compositions and methods for dyeing keratin fibers containing the 1,4-diamino-2-methoxymethylbenzene and physiologically compatible salts thereof.

2. Prior Art

A method of making substituted 1,4-diaminobenzene compounds with a substituent on the 2 position is known from U.S. Pat. No. 2,273,564, in which the corresponding nitroaniline is catalytically hydrogenated. The preparation of the 1,4-diamino-2-methoxymethyl benzene according to this process however is very expensive, since an expensive purification of the final product is required, which is also made more difficult by the oxidation sensitivity of the obtained free base.

SUMMARY OF THE INVENTION

It is an object of the present invention to provide a simple manufacturing method for making 1,4-diamino-2-methoxymethyl benzene which permits a simple production of the oxidation-insensitive salts.

It has now surprisingly been found that the 1,4-diamino-2-methoxymethyl benzene and its salts of formula (I) are obtainable from a nitrophenol of formula (IV) by reaction to the appropriate phenoxyacetamide of formula (V) and subsequently rearranging to form the nitroaniline of formula (VI) and reducing in a simple manner with good yield.

The subject matter of the present invention is thus a method for making 1,4-diamino-2-methoxymethylbenzene and its physiologically compatible salts of formula (I):

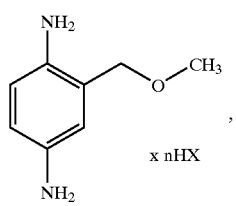

wherein n is a number from 0 to 2 and HX represents an inorganic or organic salt, which comprises a) reacting 2-methoxymethyl-4-nitrophenol of formula (IV) with chloroacetamide to form 2-(2-methoxymethyl-4-nitrophenoxy)acetamide of formula (V);

b) rearranging the 2-(2-methoxymethyl-4-nitrophenoxy) acetamide of formula (V) to form 2-methoxymethyl-4-nitroaniline of formula (VI); and then c) hydrogenating the 2-methoxymethyl-4-nitroaniline of formula (VI) catalytically to form 1,4-diamino-2-methoxmethyl benzene of formula (I) and converting with an acid to a suitable acid adduct if necessary (when n≠0).

Either inorganic or organic acids can be used as the acid ingredient. However the following acids are preferred: hydrochloric acid, sulfuric acid, boric acid, citric acid and tartaric acid. Hydrochloric and sulfuric acid are especially preferred.

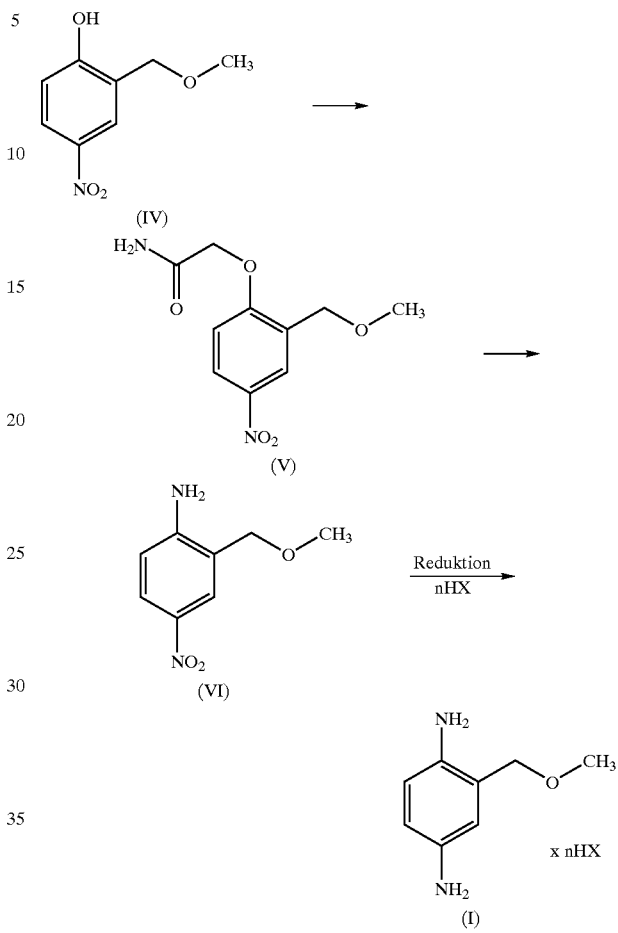

The 2-methoxymethyl-4-nitrophenol of formula (IV) is reacted with a halogen acetamide with heating. Iodoacetamide is especially suitable for this purpose however the somewhat less reactive bromoacetamide is also suitable. If the less expensive chloroacetamide is to be used instead, it is advantageous to catalyze the reaction with an iodide, such as sodium iodide or potassium iodide. The amount of the iodide that will result in a higher reaction rate is considerably more than 10% (molar); 50% (molar) has proven to be suitable throughout. The reaction can be performed easily in the usual manner in a single dipolar aprotic solvent under reflux temperature. The dipolar aprotic solvent can be, for example, acetone, a di($C_1$- to $C_6$-)alkyl ether of a mono or polyethylene glycol(e.g. an ethylene glycol dialkyl ether, a diethylene glycol dialkyl ether, a triethylene glycol dialkyl ether or a polyethylene glycol dialkyl ether). Acetone or a di($C_1$- to $C_6$-)alkyl ether of a mono or polyethylene glycol with a boiling point under 200° C., particularly ethylene glycol dimethyl ether, is preferred. The reaction of the resulting 2-(2-methoxymethyl-4-niotrophenoxy)-acetamide of formula (V) to the corresponding nitroaniline (VI) occurs by heating of the compound of formula (V) in a solvent, such as dimethylformamide, dimethylacetamide or N-methylpyrrolidone, while adding a base, analogous to the reaction described in W. R. Baker, J.Org. Chem. 48, 5140 (1983). Besides the bases disclosed in this reference carbonates, such as sodium carbonate or potassium carbonate, can be used as the added base. Since the carbonates are present in a suspension under the conditions of this latter reaction, it is advantageous to provide it as a fine powder and to use it in a two to five fold excess. The powder should be as fine as possible. The reaction can be performed in a wide temperature range. At temperatures below 80° C. the conversion is low, while at temperatures above 140° C. the reaction mixture is darkly colored by by-products, so that the preferred temperature is in a range from 80 to 120° C. The subsequent catalytic hydrogenation to 1,4-diamino-2-methoxymethylbenzene of formula (I) occurs in the usual manner at room temperature with slightly elevated hydrogen pressure or at slightly elevated temperatures over a palladium/activated charcoal catalyst. It is particularly advantageous that in the method according to the invention scarcely any interfering by-products are produced so that additional purification is not necessary. The product of formula (I) is isolated, preferably in the form of a salt with an organic or inorganic acid, especially hydrochloride or sulfuric acid, (n≠0) because of the high oxidation sensitivity of the free base. The acid is added in a slight excess considering the number of respective acid groups, so that both amine groups in the compound of formula (I) are protonated. Monobasic acids should be added in amounts of from 2 to 2.5 equivalents, while dibasic acids should be added in amounts of from 1 to 1.5. Alcohols and ether are preferred as solvents for salt formation, since generally the acids are soluble in them and adducts that are formed in them will easily crystallize out from them.

The compounds of formula (I) are outstanding as oxidation dye-precursor compounds for dyeing keratin fibers. The present invention also includes compositions and methods for dyeing keratin fibers, especially wool, silk or hair, particularly human hair, using the compounds of formula (I). Although the compounds of formula (I) are especially suitable for dyeing kertain fibers, in principle it would also be possible to dye other natural or synthetic fibers, especially cotton or nylon 66, with these compounds.

The compounds of formula (I) can be used both alone and also in combination with certain known developer substances and/or coupler substances. The following compounds especially are suitable coupler substances: N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di-[(2-hydroxyethyl)amino]-1,5-dimethoxybenzene, 2,3-diamino-6-methoxypyridine, 3-amino-6-methoxy-2-(methylamino)-pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1-(3-hydroxypropoxy)benzene, 1-(2-aminoethoxy)-2,4-diaminobenzene, 2-amiono-1-(2-hydroxyethoxy)-4-methylaminobenzene, 2,4-diaminophenoxyacetic acid, 3-[di (2-hydroxyethyl)-amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di-(2,4-diaminophenoxy) methane, 1,3-diamino-2,4-dimethoxybenzene, 2,6-bis-(2-hydroxyethyl)aminotoluene, 4-hydroxyindol, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methyl-phenol, 3-amino-phenol, 2-[(3-hydroxyphenyl)amino]acetamide, 5-[(2-hydroxy-ethyl)amino]-2-methylphenol, 3-[(2-hydroxyethyl)amino]-phenol, 3-[(2-methoxy-ethyl)amino]-phenol, 5-amino-2-ethylphenol, 2-(4-amino-2-hydroxyphenoxy)-ethanol, 5-[(3-hydroxypropyl)amino]-2-methylphenol, 3-[(2,3-dihydroxypropyl)-amino]-2-methyl-phenol, 3-[(2-hydroxyethyl)amino]-2-methylphenol, 2-amino-3-hydroxypyridine, 5-amino-4-chloro-2-methylphenol, 1-naphthol, 1,5-dihydroxy-naphthalene, 1,7-dihydroxy-naphthalene, 2,3-dihydroxynaphthalene, 2,7-dihydroxynaphthalene, 2-methyl-1-naphthol acetate, 1,3-dihydroxy-benzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxy-aniline, 5-[(2-hydroxyethyl)amino]-1,3-benzodioxole, 6-bromo-1-hydroxy-3,4-methylendioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazoleone, 5,6-dihydroxyindole, 5,6-dihydroxyindoline, 5-hydroxy-indole, 6-hydroxyindole, 7-hydroxy-indole and 2,3-indolindione, or their salts.

To produce particularly natural shades and fashionable red tones it is especially advantageous to use the compounds of formula (I) in combination with additional developer substances. The follow compounds may be considered as the developer substances: para-phenylenediamine, para-aminophenols and 4,5-diaminopyrazoles, or their salts. The following compounds are especially suitable as developer compounds: 1,4-diaminobenzene (p-phenylendiamine), 1,4-diamino-2-methylbenzene (p-toluylenediamine), 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenylaminoaniline, 4-dimethylaminoaniline, 4-diethylaminoaniline, 4-[di(2-hydroxyethyl)amino]aniline, 4-[(2-methoxyethyl)amino]-aniline, 4-[(3-hydroxypropyl)amino]aniline, 1,4-diamino-2-(2-hydroxyethyl)benzene, 1,4-diamino-2-(1-methylethyl) benzene, 1,3-bis-[(4-aminophenyl)-(2-hydroxyethyl) amino]-2-propanol, 1,8-bis-(2,5-diaminophenoxy)-3,6-dioxaoctane, 4-aminophenol, 4-amino-3-methylphenol, 4-methylaminophenol, 4-amino-2-(aminomethyl)phenol, 4-amino-2-[(2-hydroxyethyl)amino]methylphenol, 4-amino-2-(methoxymethyl)phenol, 4-amino-2-(2-hydroxyethyl)phenol, 5-amino-salicylic acid, 2,5-diaminopyridine, 2,4,5,6-tetraamino-pyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)-methyl]-1H-pyrazole, 1-[(4-chlorophenyl) methyl]-4,5-diamino-1H-pyrazole, 4,5-diamino-1-methyl-1H-pyrazole, 4,5-diamino-3-methyl-1-phenyl-1H-pyrazole, 4,5-diamino-1-(2-hydroxyethyl)-3-methyl-1H-pyrazole, 2-amino-phenol, 2-amino-6-methylphenol and 2-amino-5-methyl-phenol, or their salts.

The compounds of formula (I) can also understandably be used in combination with various direct-dyeing anionic, cationic or neutral dye compounds. The following are preferred examples of anionic dye direct-dyeing dye compounds for use in the compositions of the invention: 6-hydroxy-5-[(4-sulfophenyl)azo]-2-naphthalene sulfonic acid disodium salt (C.I. 15985; Food Yellow No. 3; FD&C Yellow No. 6), 2,4-dinitro-1-naphthol-7-sulfonic acid disodium salt (C.I.10316; Acid Yellow No. 1; Food Yellow No. 1), 2-(indan-1,3-dion-2-yl)quinoline-x,x-sulfonic acid (mixture of mono- and disulfuonic acid) (C.I.47005;D&C Yellow No. 10; Food Yellow No. 13, Acid Yellow No. 3), 5-hydroxy-1-(4-sulfophenyl)-4-[(4-sulfophenyl)azo] pyrazole-3-carboxylic acid sodium salt (C.I. 19140; Food Yellow No. 4; Acid Yellow No. 23), 9-(2-carboxyphenyl)-6-hydroxy-3H-xanthen-3-one (C.I.45350; Acid Yellow No. 73; D&C Yellow No. 8), 5-[(2,4-dinitrophenyl)amino]-2-phenylaminobenzenesulfonic acid sodium salt (C.I.10385; Acid Orange No. 3), 4-[(2,4-dihydroxyphenyl)azo]-benzene sulfonic acid monosodium salt (C.I.14270; Acid Orange No. 6), 4-[(2-hydroxynaphth-1-yl)azo]benzenesulfonic acid sodium salt (C.I. 15510; Acid Orange No. 7), 4-[(2,4-dihydroxy-3-[(2,4-dimethylphenyl)azo]phenyl)azo]-benzene sulfonic acid sodium salt (C.I.20170; Acid Orange No. 24), 4-hydroxy-3-[(4-sulfonaphth-1-yl)azo]-1-naphthalene sulfonic acid disodium salt (C.I. 14720; Acid Red No. 14), 6-hydroxy-5-[(4-sulfonaphth-1-yl)azo]-2,4-naphthalene-disulfonic acid trisodium salt (C.I. 16255; Ponceau 4R; Acid Red No. 18), 3-hydroxy-4-[(4-sulfonaphth-1-yl)azo]-2,7-naphthalene-disulfonic acid trisodium salt (C.I. 16185; Acid Red No. 27), 8-amino-1-hydroxy-2-(phenylazo)-3,6-naphthalene disulfonic acid disodium salt (C.I.17200; Acid Red No. 33), 5-(acetylamino)-4-hydroxy-3-[(2-methylphenyl)azo]-2,7-naphthalene disulfonic acid disodium salt (C.I.18065; Acid Red No. 35), 2-(3-hydroxy-2,4,5,7-tetraiodo-dibenzopyran-6-on-9-yl)-benzene sulfonic acid disodium salt (C.I. 45430; Acid Red No. 51), N-[6-(diethylamino)-9-(2,4-disulfophenyl)-3H-xanthen-3-yliden]-N-ethylethanaminium hydroxide, inner Salt, sodium salt (C.I.45100; Acid Red No. 52), 8-[(4-(phenylazo)phenyl) azo]-7-naphthol-1,3-disulfonic acid disodium salt (C.I. 27290; Acid Red No. 73), 2',4',5',7'-tetrabromo-3',6'-dihydroxyspiro[isobenzofuran-1-(3H),9'-[9H]xanthen]-3-one disodium salt (C.I.45380; Acid Red No. 87), 2',4',5',7'-tetrabromo-4,5,6,7-tetrachloro-3',6'-dihydroxyspiro [isobenzofuran-1(3H),9'[9H]xanthen]-3-one disodium salt (C.I. 45410; Acid Red No. 92), 3',6'-dihydroxy-4',5'-diiodospiro[isobenzofuran-1(3H),9'(9H)-xanthen)-3-one disodium salt (C.I. 45425; Acid Red No. 95), (2-sulfophenyl)-di-[4-(ethyl-((4-sulfophenyl)methyl)amino) phenyl]carbenium disodium salt, betaine (C.I. 42090; Acid Blue No.9; FD&C Blue No.1), 1,4-bis-[(2-sulfo-4-methyl-phenyl)amino]-9,10-anthraquinone disodium salt (C.I. 61570; Acid Green No. 25), bis-[4-(dimethylamino)phenyl]-(3,7-disulfo-2-hydroxynaphth-1-yl)carbenium inner salt, monosodium salt (C.I. 44090; Food Green No. 4; Acid Green No. 50), bis-[4-(diethylamino)phenyl](2,4-disulfophenyl)carbenium inner salt, sodium salt (2:1) (C.I. 42045; Food Blue No. 3; Acid Blue No. 1), bis[4-(diethylamino)phenyl]-(5-hydroxy-2,4-disulfophenyl) carbenium inner salt, calcium salt (2:1) (C.I. 42051; Acid Blue No. 3), 1-amino-4-(cyclohexylamino)-9,10-anthraquinone-2-sulfonic acid sodium salt (C.I. 62045; Acid Blue No. 62), 2-(1,3-dihydro-3-oxo-5-sulfo-2H-indol-2-yliden)-2,3-dihydro-3-oxo-1H-indol-5-sulfonic acid disodium salt (C.I. 73015; Acid Blue No. 74), 9-(2-carboxyphenyl)-3-[(2-methylphenyl)amino]6-[(2-methyl-4-sulfophenyl)amino]xanthylium inner salt, monosodium salt (C.I. 45190; Acid Violet No. 9), 1-hydroxy-4-[(4-methyl-2-sulfophenyl)amino]-9,10-anthraquinone sodium salt (C.I. 60730; D&C Violet No. 2; Acid Violet No. 43), bis-[3-nitro-4-[(4-phenylamino)-3-sulfophenylami no]phenyl]-sulfone (C.I. 10410; Acid Brown No. 13), 5-amino-4-hydroxy-6-[(4-nitrophenyl)azo]3-(phenylazo)-2,7-naphthalene disulfonic acid disodium salt (C.I.20470; Acid Black No. 1), 3-hydroxy-4-[(2-hydroxynaphth-1-yl)azo]-7-nitronaphthalenesulfonic acid chromium complex (3:2) (C.I. 15711; Acid Black No. 52), 3-[(2,4-dimethyl-5-sulfophenyl) azo]-4-hydroxy-1-naphthalene-sulfonic acid disodium salt (C.I. 14700; Food Red No. 1; Ponceau SX; FD&C Red No. 4), 4-(acetylamino)-5-hydroxy-6-[(7-sulfo-4-[(4-sulfophenyl)azo]naphth-1 yl)azo]-1,7-naphthalene disulfonic acid tetrasodium salt (C.I. 28440; Food Black No. 1), 3-hydroxy-4-(3-methyl-5-oxo-1-phenyl-4,5-dihydro-1H-pyrazole-4-yl-azo)-naphthalene-1-sulfonic acid sodium salt chromium complex (Acid Red No. 195).

The following are preferred cationic direct-dyeing dye compounds: 9-(dimethylamino)benzo[a]phenoxazin-7-ium chloride (C.I. 51175; Basic Blue No. 6), di[4-(diethylamino) phenyl][4-(ethylamino)naphthyl]carbenium chloride (C.I. 42595; Basic Blue No. 7), 3,7-di(dimethylamino) phenothiazin-5-ium chloride (C.I. 52015; Basic Blue No. 9), di[4-dimethylamino)phenyl][4(phenylamino)naphthyl] carbenium chloride (C.I. 44045; Basic Blue No. 26), 2-[(4-(ethyl(2-hydroxyethyl )amino)phenyl )azo]-6-methoxy-3-methylbenzothiazol ium methylsulfate (C.I. 11154; Basic Blue No. 41), 8-amino-2-bromo-5-hydroxy-4-imino-6-[(3-(trimethylammonio)phenyl)amino]-1 (4H)naphthalenone chloride (C.I.56059; Basic Blue No. 99), bis-[4-(dimethylamino)phenyl][4-(methylamino)phenyl] carbenium chloride (C.I. 42535; Basic Violet No. 1), tris-(4-amino-3-methylphenyl)carbenium chloride (C.I. 425 20; Basic Violet No. 2), tris-[4-(dimethylamino)phenyl] carbenium chloride (C.I. 42555; Basic Violet No. 3), 2-[3, 6-(diethylamino)dibenzopyranium-9-yl]benzoic acid chloride (C.I. 45170; Basic Violet No. 10), di(4-aminophenyl) (4-amino-3-methylphenyl)carbenium chloride (C.I. 42510; Basic Violet No. 14), 1,3-bis[(2,4-diamino-5-methylphenyl) azo]-3-methylbenzene (C.I. 21010;Basic Brown No. 4), 1-[(4-aminophenyl)azo]-7-(trimethylammonio)-2-naphthol chloride (C.I. 12250; Basic Brown No. 16), 1-[(4-amino-2-nitrophenyl)azo]-7-(trimethylammonio)-2-naphthol chloride (C.I. 12251; Basic Brown No.17), 1-[(4-amino-3-nitrophenyl)azo]-7-(trimethylammonio)-2-naphthol chloride (C.I. 12251; Basic Brown No. 17), 3,7-diamino-2, 8-dimethyl-5-phenylphenazinium chloride (C.I. 50240; Basic Red No. 2), 1,4-dimethyl-5-[(4(dimethylamino) phenyl)azo]-1,2,4-triazolium chloride (C.I. 11055; Basic Red No. 22), 2-hydroxy-1-[(2-methoxyphenyl)azo]-7-(trimethylammonio)naphthalene chloride (C.I. 12245; Basic Red No. 76), 2-[2-((2,4-dimethoxyphenyl)amino)ethenyl]-1,3,3-trimethyl-3H-indol-1-ium-chloride (C.I. 48055; Basic Yellow No. 11), 3-methyl-1-phenyl-4-[(3-(trimethylammonio)phenyl)azo]-pyrazole-5-one chloride (C.I. 12719; Basic Yellow No. 57), bis-[4-(diethylamino) phenyl]phenylcarbenium hydrogen sulfate(1:1) (C.I. 42040; Basic Green No. 1).

To improve the color balance and to produce special shades the following nonionic direct-dyeing dye compounds have proven to be especially useful in the compositions according to the invention: 1-amino-2-[(2-hydroxyethyl) amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl) amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No.9), 1-[(2-ureidoethyl)amino]-4-nitrobenzene, 4-[(2,3-dihydroxypropyl )amino]-3-nitro-1-trifluoromethylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 1-amino-4-[(2-hydroxyethyl)amino]-2-nitrobenzene (HC Red No. 7), 2-amino-4,6-dinitrophenol, 2-ethylamino-4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2hydroxyethyl)amino]-2-nitrobenzene, 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-[(2-aminoethyl)amino]4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino] 4,6-dinitrophenol, 4-ethylamino-3-nitrobenzoic acid, 2-[(4-amino-2-nitrophenyl)amino]-benzoic acid, 2-chloro-6-methylamino-4-nitrophenol 2-chloro-6-[(2-hydroxyethyl)amino]4-nitrophenol, 2-chloro-6-ethylamino-4-nitrophenol, 2-amino-6-chloro-4-nitrophenol, 4-[(3-hydroxypropyl )amino]-3-nitrophenol, 2,5-diamino-6-nitropyridine, 1,2,3,4-tetrahydro-6-nitrochinoxalin, 7-amino-3,4-dihydro-6-nitro-2H-1,4-benzoxazine (HC Red No. 14),1,4-bis-[(2-hydroxyethyl )amino]-2-nitrobenzene, 1-(2-hydroxyethyl )ami no-2-nitro-4-[di(2-hydroxyethyl)amino]benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl )amino]-2-nitrobenzene (HC Blue No. 11), 1-[(2,3-dihydroxy-propyl)amino]4-[methyl-(2-hydroxyethyl)amino]-2-nitrobenzene (HC Blue No. 10), 1-[(2,3-dihydroxypropyl)amino]4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2),1-methylamino-4-[methyl-(2,3-dihydroxypropyl)amino]-2nitrobenzene (HC Blue No. 6), 2-((4-amino-2-nitrophenyl)amino)-5-dimethylamino-benzoic acid (HC Blue No. 13), 1,4-di[(2,3-dihydroxypropyl)amino]-9,10-anthraquinone, 1-[(2-hydroxyethyl)amino]4-methylamino-9,10-anthraquinone (C.I. 61505, disperse Blue No. 3), 2-[(2-aminoethyl)amino]-9,10-anthraquinone (HC Orange No. 5),1-hydroxy-4-[(4-methyl-2-sulfophenyl)amino]-9,10-anthraquinone, 1-[(3-aminopropyl)amino]4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (C.I.62015, disperse Red No. 11, Solvent Violet No. 26), 1,4-dihydroxy-5,8-bis[(2-hydroxyethyl)amino-9,10-anthraquinone (C.I. 62500, disperse Blue No. 7, Solvent Blue No. 69), 1-[di-(2-hydroxyethyl)amino]-3-methyl-4-[(4-nitrophenyl)azo] benzene (C.I. 11210, disperse Red No. 17), 4-[(4-aminophenyl)azo]-1-[di(2-hydroxyethyl)amino]-3-methylbenzene (HC Yellow No. 7), 2,6-diamino-3-[(pyridine-3-yl)azo]pyridine, 2-((4-(acetylamino)phenyl) azo)-4-methylphenol (C.I. 11855; disperse Yellow No. 3).

From the group of direct-dyeing dye compounds the following compounds have a special significance: 2-amino-4,6-dinitrophenol, 2-ethylamino-4,6-dinitrophenol, 2-[(2-hydroxyethyl)amino]4,6-dinitrophenol and dye compounds of the following general formula (VII):

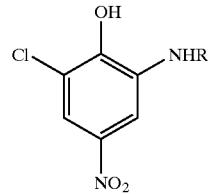

(VII)

wherein R represents hydrogen, methyl, ethyl or hydroxyethyl.

The above-described combination according to the invention of the compounds of formula (I) with oxidation dye precursor compounds and/or direct-dyeing dye compounds is applied to the fibers to be dyed in a suitable dye-carrying composition.

The present invention also includes ready-to-apply hair dye mixtures for oxidative dyeing of hair, which are each made by mixing an oxidation dye precursor composition with an oxidizing agent immediately prior to application. They are characterized by a content of at least one compound of formula (I) as well as additional oxidation dye precursor compounds and/or direct-dyeing dye compounds as needed.

The compounds of formula (I) and the oxidation dye precursor compounds are contained in the compositions of the invention in total amounts of about 0.01 to 10 percent by weight respectively, preferably from 0.2 to 6 percent by weight. The total concentration of direct-dyeing dye compounds in the compositions according to the invention amounts to about 0.1 to 10 percent by weight respectively, preferably from 0.1 to 5 percent by weight.

Furthermore antioxidants, perfume oils, complex formers, wetting agents, emulsifiers, penetration agents, buffer systems, preservatives, thickeners, care materials and other cosmetic additives may be present in the dye-carrying or oxidation dye precursor composition according to the invention.

The form of the oxidation dye precursor composition and also for the ready-to-apply dye mixture can be, for example, a solution, especially an aqueous or aqueous-alcoholic solution. However the particularly preferred form of the composition according to the invention is a cream, a gel or an emulsion. Its composition comprises a mixture of the dye ingredients with the conventional additive ingredients usually used in this type of preparation.

The conventional additive ingredients for solutions, creams, emulsion or gels are, for example, solvents, such as water, lower aliphatic alcohols, for example ethanol, n-propanol and isopropanol or glycols, such as glycerol and 1,2-propylene glycol; wetting agents or emulsifiers from the classes of anionic, cationic, amphoteric or nonionic surface-active substances, such as fatty alcohol sulfates, ethoxylated fatty alcohol sulfates, alkyl sulfonates, alkyl benzene sulfonates, alkyltrimethylammonium salts, alkyl betaines, ethoxylated fatty alcohols, ethoxylated nonylphenols, fatty acid alkanol amides, fatty acid esters; thickeners, such as higher fatty alcohols, starches or cellulose derivative compounds, petrolatum (Vaseline®), paraffin oils and fatty acids and furthermore care materials, such as cationic resins, lanolin derivative compounds, cholesterol, pantothenic acid and betain. The above-mentioned ingredients are included in the compositions according to the invention in respective amounts suitable for their purposes. For example, the wetting agents and emulsifiers are contained in the compositions according to the invention in concentrations of about 0.5 to 30 percent by weight, the thickeners in amounts of from about 0.1 to 25 percent by weight and the care materials in a concentration of about 0.1 to 5.0 percent by weight.

The ready-to-apply hair dye mixture according to the invention is made by a method comprising mixing the oxidation dye precursor composition with a liquid oxidizing agent immediately prior to application.

Hydrogen peroxide, or its addition compounds with urea, melamine or sodium bromate, in the form of a 1 to 12 percent by weight, preferably 6 percent by weight, aqueous solution, is preferred as the oxidizing agent. Hydrogen peroxide is especially preferred.

The oxidation dye precursor composition and the oxidizing agent are mixed with each other in a weight ratio of from 5:1 to 1:3. A weight ratio of 1:1 to 1:2 is especially preferred.

The pH of the ready-to-apply hair dye mixture according to the invention is adjusted during the mixing of the preferred alkaline oxidation dye precursor composition with the mostly acidic oxidizing agent. The resulting pH value of the mixture is determined by the alkali content of the dye-carrying or oxidation dye precursor composition, the acid content of the oxidizing agent and the mixing ratio. The pH of the ready-to-apply hair dye composition amounts to about 3 to 11, preferably between 6 and 10.5.

The pH values of both the oxidation dye precursor composition and the oxidizing agent-containing composition can both be adjusted by adding dilute organic or inorganic acids, such as phosphoric acid, ascorbic acid and lactic acid, or bases, such as monoethanolamine, triethanolamine, 2-amino-2-methyl-1-propanol, ammonia, sodium hydroxide, potassium hydroxide or tris(hydroxymethyl) aminomethane.

After mixing the above-described oxidation dye precursor composition with an oxidizing agent, an amount of the ready-to-apply hair dye mixture sufficient for dyeing the hair, generally from about 60 to 200 grams, is applied to the hair.

The hair dye mixture is allowed to act on the hair after application for about 10 to 45 minutes at 15 to 50° C., preferably for 30 minutes at 40° C. It is subsequently rinsed from the hair with water. If necessary the hair is washed with a shampoo after rinsing with water and perhaps with a dilute weak organic acid, for example citric or tartaric acid. Subsequently the hair is dried.

The following examples illustrate the above-described invention, but without however limiting the broad concept of the invention.

EXAMPLES

Example 1

Preparation of 1,4-diamino-2-methoxymethylbenzene dihydrochloride

Step 1: 2-(2-methoxymethyl-4-nitrophenoxy) acetamide 25 g of 2-methoxymethyl-4-nitrophenol, 14 g of chloroacetamide, 18.9 g of calcium carbonate, and 12.5 g of potassium iodide in a 150 ml of acetone are heated under reflux for four hours. Subsequently the reaction mixture is cooled to room temperature and poured into water. The resulting precipitate is filtered, washed with water and subsequently dried. 20 g of a pale yellow product is obtained having a melting point of from 157 to 158° C.

$^1$H-NMR (DMSO-d$_6$): δ=3.40 ppm(s,3H); 4.60 ppm (s,2H); 4.65 ppm(s,2H); 7.09 ppm (d, $^3J_{HH}$=9.1 Hz,1H); 7.47 ppm (s broad,2H); 8.15 ppm (d,$^4J_{HH}$=2.55 Hz,1H); 8.18 ppm (dd, $^3J_{HH}$=9.1 Hz, $^4J_{HH}$=2.55 Hz,1H).

CHN analysis (C$_{10}$H$_{12}$N$_2$O$_5$; MW=240.21)

|  | % C | % H | % N |
|---|---|---|---|
| Calculated: | 50.00 | 5.04 | 11.66 |
| Found: | 50.10 | 5.05 | 11.43 |

Step 2: 2-methoxymethyl-4-nitroaniline 20 g of the 2-(2-methoxymethyl-4-nitrophenoxy) acetamide made in step 1 are dissolved in 55 ml of N-methylpyrrolidone, mixed with 29 g of potassium carbonate and heated for 3 hours at 100° C. Subsequently the reaction mixture is cooled to room temperature and the solvent is removed in vacuum at 60 to 80° C. The remaining residue is crystallized by addition of 100 ml water. 8.8 g of a yellowish product are obtained with a melting point of 90 to 92° C.

$^1$H-NMR (DMSO-d$_6$): δ=3.30 ppm(s,3H); 4.35 ppm (s,2H); 6.51 ppm (s broad, 2H); 6.68 ppm (d,$^3J_{HH}$=8.85 Hz,1H); 7.92 ppm (dd,$^3J_{HH}$=8.85 Hz, $^4J_{HH}$=2.6 Hz,1H); 7.98 ppm (d,$^4J_{HH}$=2.6 Hz,1H).

CHN analysis (C$_8$H$_{10}$N$_2$O$_3$; MW=182.18)

|  | % C | % H | % N |
|---|---|---|---|
| Calculated: | 52.74 | 5.53 | 15.38 |
| Found: | 52.77 | 5.63 | 15.17 |

Step 3: 1,4-diamino-2-methoxymethylbenzene dihydrochloride 8 g of the 2-methoxymethyl-4-nitroaniline made in step 2 are dissolved in 100 ml ethanol, mixed with 0.8 g palladium (10% in activated carbon) and hydrogenated under mildly elevated hydrogen pressure. After about 6 hours the hydrogen uptake has ended and a colorless solution is obtained after removal of the catalyst by filtration. The hydrochloride precipitates when hydrogen chloride gas is conducted into the reaction mixture. The precipitate is filtered with suction, washed with a little ethanol and dried in vacuum. 7.2 g of bright beige crystals result with a melting point of over 280° C.

$^1$H-NMR (DMSO-d$_6$): δ=3.35 ppm(s,3H); 4.55 ppm (s,2H); 7.27 ppm (dd, $^3J_{HH}$=8.30 Hz, $^4J_{HH}$=2.30 Hz,1H); 7.33 ppm (d, $^4J_{HH}$=2.6 Hz,1H); 7.36 ppm (d, $^3J_{HH}$=8.30 Hz,1H); 9.37 ppm (s, very broad, 6H+water).

CHN analysis (C$_8$H$_{12}$N$_2$O×2HCl; MW=225.12)

|  | % C | % H | % N |
|---|---|---|---|
| Calculated: | 42.68 | 6.27 | 12.44 |
| Found: | 42.80 | 6.39 | 12.03 |

Example 2

Preparation of 1,4-diamino-2-methoxymethylbenzene sulfate 3.65 g of the 2-methoxymethyl-4-nitroaniline made in step 2 of example 1 are dissolved in 35 ml tetrahydrofuran, mixed with 0.3 g palladium (10% in activated carbon) and hydrogenated under slightly elevated hydrogen pressure. After about 5 hours the hydrogen uptake has ended and a colorless solution is obtained after removal of the catalyst by filtration. The acid adduct precipitates by addition of 1.2 g of sulfuric acid in 50 ml tetrahydrofuran. The precipitate is filtered with suction, washed with a little tetrahydrofuran and dried in vacuum. 3.3 g of bright beige crystals result with a melting point of 206 to 212° C.

$^1$H-NMR (DMSO-d: δ=3.30 ppm(s,3H); 4.32 ppm (s,2H); 6.79 ppm (d, $^3J_{HH}$=8.55 Hz,1H); 6.89 ppm (d broadened, $^3J_{HH}$=8.55 Hz); 6.95 ppm (s broadened, 1H).

CHNS analysis ($C_8H_{12}N_2O \times H_2SO_4$; MW=250.27)

Accounting for 1.21% crystallization water:

|  | % C | % H | % N | % S |
|---|---|---|---|---|
| Calculated: | 37.93 | 5.71 | 11.06 | 12.66 |
| Found: | 37.70 | 5.60 | 10.90 | 13.00 |

Example 3
Hair Dye Precursor Composition, Basic Cream

| | |
|---|---|
| 15.00 g | cetyl stearyl alcohol (50/50) |
| 5.00 g | glycerol monostearate |
| 2.00 g | cocamide DEA |
| 10.00 g | sodium lauryl ether sulfate, 28% aqueous solution |
| 0.30 g | ascorbic acid |
| 0.40 g | sodium sulfite |
| 4.50 g | ammonia, 25% aqueous solution |
| 0.56 g | 1,4-diamino-2-methoxymethylbenzene dihydrochloride |
| X g | coupler substance from Table I |
| to 100.00 g | water, demineralized. |

The pH of the cream is between 10 and 10.5.

Immediately prior to application 100 g of the above-described oxidation dye precursor composition is mixed with 100 grams of a 6% by weight aqueous hydrogen peroxide solution. The resulting ready-to-apply hair dye mixture is applied to bleached hair in the required amount. After an acting time of 30 minutes at 40° C. the hair is washed with a shampoo, rinsed with water and dried. The obtained color shades and color intensities are summarized in Table I.

TABLE I

HAIR DYE PRECURSOR COMPOSITIONS CONTAINING 1,4-DIAMINO-2-METHOXYMETHYLBENZENE DIHYDROCHLORIDE

| Example | Coupler Compound | Color Shade | Intensity |
|---|---|---|---|
| 3a | 0.28 g resorcinol | Medium blond | (++) |
| 3b | 0.27 g 3-aminophenol | Gray-brown | (o) |
| 3c | 0.31 g 5-amino-2-methylphenol | Red-violet | (++) |
| 3d | 0.64 5-((2-hydroxyethyl)amino)-2-methoxyaniline dihydrochloride | Bluish-black | (++) |
| 3e | 0.47 g 6-amino-3,4-dihydro-2H-1,4-benzoxazine hydrochloride | Bluish-black | (++) |
| 3f | 0.59 g 1,3-diamino-4-methoxybenzene sulfate | Blue | (++) |
| 3g | 0.36 g 1-chloro-2,4-dihydroxybenzene | Gold | (++) |
| 3h | 0.57 g 3-amino-6-methoxy-2-(methylamino)pyridine hydrochloride | Dark aubergine | (++) |
| 3i | 0.35 g 5-hydroxy-1,3-benzodioxole | Chestnut | (++) |

TABLE I-continued

HAIR DYE PRECURSOR COMPOSITIONS CONTAINING 1,4-DIAMINO-2-METHOXYMETHYLBENZENE DIHYDROCHLORIDE

| Example | Coupler Compound | Color Shade | Intensity |
|---|---|---|---|
| 3j | 0.43 g 5-amino-1,3-benzodioxole hydrochloride | Dark brown | (++) |
| 3k | 0.44 g 4-methoxy-1-naphthol | Aubergine | (o) |
| 3l | 0.61 g 3,5-diamino-2,6-methoxy-pyridine dihydrochloride | Bluish-black | (++) |
| 3m | 0.40 g 1,7-dihydroxynaphthalene | Blue-violet | (o) |
| 3n | 0.31 g 1,3-dihydroxy-2-methylbenzene | Red-brown | (+) |
| 3o | 0.45 g 3-dimethylaminophenylurea | Anthracite | (++) |
| 3p | 0.33 g 4-hydroxyindole | Black-violet | (++) |
| 3q | 0.39 g 3-amino-2-chloro-6-methyl-phenol | Red-violet | (++) |
| 3r | 0.56 g 2-chloro-5-((2,2,2-trifluoro-ethyl)amino)phenol | Blue-violet | (+) |
| 3s | 0.45 g 3-amino-2,4-dichlorophenol | Blue-black | (++) |
| 3t | 0.36 g 3-amino-2-chlorophenol | Blue-violet | (++) |

(o) = average
(+) = intense
(++) = very intense

Example 4
Hair Dye Precursor Composition, Acidic Cream

| | |
|---|---|
| 15.00 g | cetyl stearyl alcohol (50/50) |
| 5.00 g | glycerol monostearate |
| 2.00 g | cocamide DEA |
| 10.00 g | sodium lauryl ether sulfate, 28% aqueous solution |
| 0.30 g | ascorbic acid |
| 0.40 g | sodium sulfite |
| 0.62 g | 1,4-diamino-2-methoxymethylbenzene sulfate |
| X g | coupler substance from Table II |
| to 100.00 g | water, demineralized. |

Immediately prior to application 100 g of the above-described oxidation dye precursor composition is mixed with 100 grams of a 6% by weight aqueous hydrogen peroxide solution. The resulting ready-to-apply hair dye mixture is applied to bleached hair in the required amount. After an acting time of 30 minutes at 40° C. the hair is washed with a shampoo, rinsed with water and dried. The obtained color shades and color intensities are summarized in Table II together with the pH values.

TABLE II

HAIR DYE PRECURSOR COMPOSITIONS CONTAINING 1,4-DIAMINO-2-METHOXYMETHYLBENZENE SULFATE

| Example | Coupler | pH Value | Color Shade | Intensity |
|---|---|---|---|---|
| 4a | 0.28 g resorcinol | 6.6 | Brown | (+) |
| 4b | 0.27 g 3-aminophenol | 5.8 | Medium blond | (o) |
| 4c | 0.31 g 5-amino-2-methylphenol | 6.6 | Red-violet | (+) |
| 4d | 0.64 5-((2-hydroxyethyl)amino)-2-methoxyaniline sulfate hydrate | 6.7 | Blue | (+) |

(o) = average
(+) = intense
(++) = very intense

Example 5

Hair Dye Precursor Composition in Gel Form

| | | |
|---|---|---|
| 15.00 | g | oleic acid |
| 3.00 | g | glycerol |
| 7.00 | g | isopropanol |
| 0.50 | g | ascorbic acid |
| 0.40 | g | sodium sulfite |
| 0.40 | g | sodium hydroxide |
| 10.00 | g | ammonia, 25% aqueous solution |
| 0.56 | g | 1,4-diamino-2-methoxymethylbenzene dihydrochloride |
| X | g | coupler substance from Table III |
| to 100.00 | g | water, demineralized. |

Immediately prior to application 100 g of the above-described oxidation dye precursor composition is mixed with 100 grams of a 6% by weight aqueous hydrogen peroxide solution. The resulting ready-to-use hair dye mixture is applied to bleached hair in the required amount. After an acting time of 30 minutes at 40° C. the hair is washed with a shampoo, rinsed with water and dried. The obtained color shades, color intensities and pH are summarized in Table III.

TABLE III

HAIR DYE PRECURSOR COMPOSITIONS CONTAINING 1,4-DIAMINO-2-METHOXYMETHYLBENZENE DIHYDROCHLORIDE

| Example | Coupler | pH Value | Color Shade | Intensity |
|---|---|---|---|---|
| 5a | 0.28 resorcinol | 10.0 | Medium blond | (++) |
| 5b | 0.27 g 3-aminophenol | 9.9 | Rose | (+) |
| 5c | 0.31 g 5-amino-2-methylphenol | 10.2 | Red-violet | (+) |
| 5d | 0.64 5-((2-hydroxy-ethyl)amino)-2-methoxyaniline sulfate hydrate | 10.6 | Blue | (++) |

(o) = average
(+) = intense
(++) = very intense

Example 6

Hair Dye Solution with a Basic pH

| | | |
|---|---|---|
| 10.00 | g | ethanol |
| 10.00 | g | sodium lauryl ether sulfate, 28% aqueous solution |
| 10.00 | g | ammonia, 25% aqueous solution |
| 0.30 | g | ascorbic acid |
| 0.62 | g | 1,4-diamino-2-methoxymethylbenzene sulfate |
| X | g | coupler substance from Table IV |
| to 100.00 | g | water, demineralized. |

Immediately prior to application 10 g of the above-described oxidation dye precursor-containing solution is mixed with 10 grams of a 6% by weight aqueous hydrogen peroxide solution. The resulting ready-to-apply hair dye mixture is applied to bleached hair in the required amount. After an acting time of 30 minutes at 40° C. the hair is washed with a shampoo, rinsed with water and dried. The obtained color shades, color intensities and pH are summarized in Table IV.

TABLE IV

HAIR DYE SOLUTIONS CONTAINING 1,4-DIAMINO-2-METHOXYMETHYLBENZENE SULFATE

| Example | Coupler | pH Value | Color Shade | Intensity |
|---|---|---|---|---|
| 6a | 0.66 g 1,3-diamino-4-(2-hydroxyethoxy)-benzene sulfate | 10.7 | Blue | (+) |
| 6b | 0.39 g 3-amino-2-chloro-6-methylphenol | 10.5 | Violet | (+) |
| 6c | 0.45 g 3-amino-2,4-dichlorophenol | 10.6 | Aubergine | (+) |
| 6d | 0.56 2-chloro-5-((2,2,2-trifluoro-ethyl)amino)phenol | 10.7 | Blue | (+) |
| 6e | 0.61 3-amino-6-methoxy-2-methylamino-pyridine dihydrochloride | 10.6 | Blue-green | (+) |
| 6f | 0.36 g 1-naphthol | 10.9 | Blue-violet | (+) |

(o) = average
(+) = intense
(++) = very intense

Example 7

Hair Dye Solution with a Basic pH

| | | |
|---|---|---|
| 10.00 | g | ethanol |
| 10.00 | g | sodium lauryl ether sulfate, 28% aqueous solution |
| 10.00 | g | ammonia, 25% aqueous solution |
| 0.30 | g | ascorbic acid |
| 0.38 | g | 1,4-diamino-2-methoxymethylbenzene dihydrochloride |
| X | g | coupler substance from Table V |
| to 100.00 | g | water, demineralized. |

Immediately prior to application 10 g of the above-described oxidation dye precursor-containing solution is mixed with 10 grams of a 6% by weight aqueous hydrogen peroxide solution. The resulting ready-to-use hair dye mixture is applied to bleached hair in the required amount. After an acting time of 30 minutes at 40° C. the hair is washed with a shampoo, rinsed with water and dried. The obtained color shades, color intensities and pH are summarized in Table V.

TABLE V

HAIR DYE SOLUTIONS CONTAINING 1,4-DIAMINO-2-METHOXYMETHYLBENZENE DIHYDROCHLORIDE

| Example | Coupler | pH Value | Color Shade | Intensity |
|---|---|---|---|---|
| 7a | 0.40 g 1,3-diamino-4-(2-hydroxyethoxy)-benzene dihydrochloride | 10.5 | Blue | (+) |
| 7b | 0.26 g 3-amino-2-chloro-6-methylphenol | 10.5 | Violet | (o) |
| 7c | 0.30 g 3-amino-2,4-dichlorophenol | 10.6 | Aubergine | (o) |
| 7d | 0.37 2-chloro-5-((2,2,2-trifluoro-ethyl)amino)phenol | 10.4 | Blue | (o) |

TABLE V-continued

HAIR DYE SOLUTIONS CONTAINING 1,4-DIAMINO-2-METHOXYMETHYLBENZENE DIHYDROCHLORIDE

| Example | Coupler | pH Value | Color Shade | Intensity |
|---|---|---|---|---|
| 7e | 0.40 3-amino-6-methoxy-2-methylamino)-pyridine dihydrochloride | 10.4 | Blue-green | (o) |
| 7f | 0.24 g 1-naphthol | 10.5 | Blue-violet | (+) |

(o) = average
(+) = intense
(++) = very intense

Example 8
Dyeing Agent

A ready-to-apply dye mixture according to example 3 is applied to the textiles listed in Table VI. After an acting time of 30 minutes at 40° C., the mixture is neutralized and rinsed out with water.

TABLE VI

COLORS AND INTENSITIES OBTAINED BY DYEING VARIOUS TEXTILE FIBERS WITH EXEMPLARY COMPOSITIONS 3a, 3b, 3c and 3d

| Example | Textile Fibers | 3a | 3b | 3c | 3d |
|---|---|---|---|---|---|
| 8a | Cotton | medium brown (+) | bright brown (+) | rosé (o) | blue-gray (+) |
| 8b | Silk | medium brown (+) | brown (++) | rosé (++) | blue (+) |
| 8c | Wool | carmel (++) | dark brown (++) | red-violet (++) | blue-black (++) |
| 8d | Nylon 66 | medium blond (+) | bright brown (+) | red-brown (+) | aubergine (+) |

(o) = average
(+) = intense
(++) = very intense

Example 9
Hair Dye Precursor Composition in Gel Form

| | |
|---|---|
| 15.25 g | oleic acid |
| 3.15 g | glycerol |
| 7.80 g | ethanol |
| 0.50 g | ascorbic acid |
| X g | dye substances from Table VII |
| 10.40 g | ammonia, 25% aqueous solution |
| to 100.00 g | water, demineralized. |

Immediately prior to application 100 g of the above-described oxidation dye precursor composition is mixed with 100 grams of a 6% by weight aqueous hydrogen peroxide solution. The resulting ready-to-apply hair dye mixture is applied to bleached hair in the required amount. After an acting time of 30 minutes at 40° C. the hair is washed with a shampoo, rinsed with water and dried. The obtained color shades and color intensities are summarized in Table VII.

TABLE VII

HAIR DYE PRECURSOR COMPOSITIONS CONTAINING THE FOLLOWING DYE COMPOUNDS

| DYE COMPOUND/EXAMPLE | 9a | 9b | 9c | 9d |
|---|---|---|---|---|
| 1,4-diamino-2-methoxymethyl-benzene dihydrochloride | 0.26 g | 1.00 g | 2.25 g | 1.30 g |
| 1,4-diamino-2-methylbenzene sulfate | — | 1.00 g | — | — |
| 1,4-diamino-2-(2-hydroxyethyl)-benzene sulfate | 0.20 g | — | 0.42 g | — |
| 4-amino-3-methylphenol | 0.05 g | 0.15 g | 0.15 g | — |
| 4,5-diamino-1-(2-hydroxyethyl)-1H-pyrazole sulfate | 0.50 g | — | 0.10 g | — |
| 1,3-diamino-4-(2-hydroxyethoxy)-benzene sulfate | — | 0.20 g | — | — |
| 1,3-diamino-4-(3-hydroxypropoxy)-benzene dihydrochloride | — | — | 0.52 g | 0.10 g |
| 5-((2-hydroxyethyl)amino)-2-methoxyaniline sulfate | — | 0.10 g | — | — |
| 1-(2-hydoxyethylamino)-3,4-methylenedioxobenzene | — | 0.20 g | 0.34 g | 0.50 g |
| resorcinol | 0.15 g | 0.21 g | 0.21 g | — |
| 2-methylresorcinol | — | 0.25 g | 0.10 g | — |
| 5-amino-2-methylphenol | — | 0.20 g | 0.10 g | 0.18 g |
| 3-aminophenol | 0.34 g | 0.52 g | 0.52 g | — |
| 2-amino-6-chloro-4-nitrophenol | — | 0.24 g | 0.24 g | 0.16 g |
| 2-chloro-6-(ethylamino)-4-nitrophenol | 0.10 g | — | 0.78 g | — |
| COLORS OBTAINED | Ruby-Red | Dark brown | Rose | Medium brown |

Example 10
Hair Dye Precursor Composition, Basic Cream

| | |
|---|---|
| 15.00 g | cetyl stearyl alcohol (50/50) |
| 5.00 g | glycerol monostearate |
| 10.00 g | sodium lauryl ether sulfate, 28% aqueous solution |
| 0.30 g | sodium sulfite |
| 5.00 g | ammonia, 25% aqueous solution |
| X g | dye substances from Table VIII |
| to 100.00 g | water, demineralized. |

Immediately prior to application 100 g of the above-described oxidation dye precursor composition is mixed with 100 grams of a 6% by weight aqueous hydrogen peroxide solution. The resulting ready-to-apply hair dye mixture is applied to bleached hair in the required amount. After an acting time of 30 minutes at 40° C. the hair is washed with a shampoo, rinsed with water and dried. The obtained color shades and color intensities are summarized in Table VIII.

TABLE VIII

HAIR DYE PRECURSOR COMPOSITIONS CONTAINING THE FOLLOWING DYE COMPOUNDS

| DYE COMPOUND/EXAMPLE | 10a | 10b | 10c | 10d |
|---|---|---|---|---|
| 1,4-diamino-2-methoxymethyl-benzene sulfate | 3.00 g | 0.13 g | 0.13 g | 1.45 g |
| 5-((2-hydroxyethyl)amino)-2-methoxyaniline sulfate | 0.36 g | — | — | — |
| 1,4-diamino-2-(2-hydroxyethyl)-benzene sulfate | 0.13 g | — | 0.64 g | — |

TABLE VIII-continued

HAIR DYE PRECURSOR COMPOSITIONS CONTAINING THE FOLLOWING DYE COMPOUNDS

| DYE COMPOUND/ EXAMPLE | 10a | 10b | 10c | 10d |
|---|---|---|---|---|
| 1-(2-hydoxyethylamino)-3,4-methylenedioxobenzene | 0.20 g | 0.10 g | 0.10 g | 0.43 g |
| 4-amino-3-methylphenol | 0.17 g | 0.83 g | 0.83 g | 0.07 g |
| 2-methylresorcinol | 0.30 g | 0.30 g | 0.30 g | — |
| 3-aminophenol | 0.56 g | — | — | 0.16 g |
| 2-amino-6-chloro-4-nitrophenol | 0.35 g | 0.27 g | 0.27 g | 0.10 g |
| 1-naphthol | — | 0.04 g | 0.04 g | — |
| COLORS OBTAINED | Black | Medium brown | Dark brown | Dark brown |

Unless otherwise indicated all percentages are percentages by weight.

The disclosure in German Patent Application 199 57 282.8 of Nov. 29, 1999 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in methods of making 1,4-diamino-2-methoxymethylbenzene and physiologically compatible salts thereof as well as compositions and methods for dyeing keratin fibers containing the 1,4-diamino-2-methoxymethylbenzene and physiologically compatible salts thereof it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:

1. A ready-to-apply hair dye mixture made by a method comprising the steps of:
   a) providing an oxidation dye precursor composition containing at least one coupler compound and at least one developer compound, said at least one developer compound including at least one member selected from the group consisting of 1,4-diamino-2-methoxymethylbenzene and physiologically compatible salts of said 1,4-diamino-2-methoxymethylbenzene;
   b) mixing the oxidation dye precursor composition provided in step a) with an oxidizing agent immediately prior to application to form the ready-to-apply hair dye mixture.

2. The ready-to-apply hair dye mixture as defined in claim 1, wherein said at least one developer compound includes at least one ingredient selected from the group consisting of p-phenylenediamine, substituted p-phenylenediamine compounds besides said 1,4-diamino-2-methoxymethylbenzene and said salts thereof, aminophenols, substituted aminophenols and substituted 4,5-diaminopyrazole compounds.

3. The ready-to-apply hair dye mixture as defined in claim 1, wherein said at least one coupler compound and said at least one developer compound are present in a total amount of from 0.01 to 10 percent by weight.

4. The ready-to-apply hair dye mixture as defined in claim 1, wherein the oxidation dye precursor composition includes at least one direct-dyeing dye compound.

5. The ready-to-apply hair dye mixture as defined in claim 4, wherein the at least one direct-dyeing dye compound is present in a total amount of from 0.1 to 10 percent by weight.

6. The ready-to-apply hair dye mixture as defined in claim 1, wherein the oxidation dye precursor composition and the oxidizing agent are mixed with each other in a weight ratio of from 5:1 to 1:3 during the mixing.

7. The ready-to-apply hair dye mixture as defined in claim 1, having a pH of from 6to 10.5.

8. An aqueous or aqueous-alcoholic oxidation dye precursor composition comprising water, at least one coupler compound and at least one developer compound, said at least one developer compound including at least one member selected from the group consisting of 1,4-diamino-2-methoxymethylbenzene and physiologically compatible salts of said 1,4-diamino-2-methoxymethylbenzene.

9. The aqueous or aqueous-alcoholic oxidation dye precursor composition as defined in claim 8, wherein said at least one developer compound and said at least one coupler compound are present in a total amount of from 0.01 to 10 percent by weight.

10. The aqueous or aqueous-alcoholic oxidation dye precursor composition as defined in claim 8, wherein said at least one developer compound includes at least one ingredient selected from the group consisting of p-phenylenediamine, substituted p-phenylenediamine compounds besides said 1,4-diamino-2-methoxymethylbenzene and said salts thereof, aminophenols, substituted aminophenols and substituted 4,5-diaminopyrazole compounds.

11. The aqueous or aqueous-alcoholic oxidation dye precursor composition as defined in claim 8, further comprising from 0.1 to 10 percent by weight of at least one direct-dyeing dye compound selected from the group consisting of anionic direct-dyeing dye compounds, cationic direct-dyeing dye compounds and neutral direct-dyeing dye compounds.

12. The aqueous or aqueous-alcoholic oxidation dye precursor composition as defined in claim 8, wherein said at least one coupler compound is selected from the group consisting of 1,4-diaminobenzene, 1,4-diamino-2-methylbenzene, 1,4-diamino-2,6-dimethyl-benzene, 1,4-diamino-2,5-dimethylbenzene, 1,4-diamino-2,3-dimethylbenzene, 2-chloro-1,4-diaminobenzene, 4-phenylaminoaniline, 4-dimethylaminoaniline, 4-diethylaminoaniline, 4-[di(2-hydroxyethyl)amino]aniline, 4-[(2-methoxyethyl)-amino]-aniline, 4-[(3-hydroxypropyl)amino]aniline, 1,4-diamino-2-(2-hydroxy-ethyl)benzene, 1,4-diamino-2-(1-methylethyl)benzene, 1,3-bis-[(4-aminophenyl)-(2-hydroxyethyl)amino]-2-propanol, 1,8-bis-(2,5-diaminophenoxy)-3,6-dioxaoctane, 4-aminophenol, 4-amino-3-methylphenol, 4-methylaminophenol, 4-amino-2-(aminomethyl)phenol, 4-amino-2-[(2-hydroxyethyl)amino]methyl-phenol, 4-amino-2-(methoxymethyl)phenol, 4-amino-2-(2-hydroxyethyl)phenol, 5-amino-salicylic acid, 2,5-diaminopyridine, 2,4,5,6-tetraamino-pyrimidine, 2,5,6- triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)-methyl]-1H-pyrazole, 1-[(4-chlorophenyl)methyl]-4,5-diamino-1H-pyrazole, 4,5-diamino-1-methyl-1H-pyrazole, 4,5-diamino-3-methyl-1-phenyl-1H-pyrazole, 4,5-diamino-1-(2-hydroxyethyl)-3-methyl-1H-pyrazole, 2-amino-phenol, 2-amino-6-methylphenol and 2-amino-5-methylphenol and salts thereof.

13. The aqueous or aqueous-alcoholic oxidation dye precursor composition as defined in claim 8, further comprising at least one cosmetic additive selected from the group consisting of organic solvents, anionic surfactants, cationic surfactants, nonionic surfactants, amphoteric surfactants, thickeners, care materials, antioxidants, perfume oils, buffer systems and preservatives.

\* \* \* \* \*